United States Patent
Ben-Sasson

(10) Patent No.: US 12,097,179 B2
(45) Date of Patent: Sep. 24, 2024

(54) CARBAZOLE DERIVATIVES FOR THE TREATMENT OF FIBROTIC DISEASES AND RELATED SYMPTOMS, AND CONDITIONS THEREOF

(71) Applicant: Raziel Therapeutics Ltd., Rehovot (IL)

(72) Inventor: Shmuel Ben-Sasson, Jerusalem (IL)

(73) Assignee: RAZIEL THERAPEUTICS LTD., Rehovot (IL)

( * ) Notice: Subject to any disclaimer, the term of this patent is extended or adjusted under 35 U.S.C. 154(b) by 225 days.

(21) Appl. No.: 17/516,556

(22) Filed: Nov. 1, 2021

(65) Prior Publication Data

US 2022/0117935 A1 Apr. 21, 2022

Related U.S. Application Data

(60) Continuation of application No. 16/826,632, filed on Mar. 23, 2020, now Pat. No. 11,191,748, which is a division of application No. 15/736,307, filed as application No. PCT/IL2016/050624 on Jun. 14, 2016, now Pat. No. 10,632,102.

(60) Provisional application No. 62/175,552, filed on Jun. 15, 2015.

(51) Int. Cl.
| | | |
|---|---|---|
| A61K 31/403 | (2006.01) | |
| A61K 9/00 | (2006.01) | |
| A61K 31/14 | (2006.01) | |
| A61K 45/06 | (2006.01) | |
| A61P 17/02 | (2006.01) | |
| A61P 41/00 | (2006.01) | |

(52) U.S. Cl.
CPC .......... *A61K 31/403* (2013.01); *A61K 9/0014* (2013.01); *A61K 9/0024* (2013.01); *A61K 9/0029* (2013.01); *A61K 31/14* (2013.01); *A61K 45/06* (2013.01); *A61P 17/02* (2018.01); *A61P 41/00* (2018.01)

(58) Field of Classification Search
CPC .............................. A61K 31/14; A61K 31/403
See application file for complete search history.

(56) References Cited

U.S. PATENT DOCUMENTS

| | | | |
|---|---|---|---|
| 2,590,125 | A | 3/1952 | Robinson et al. |
| 2,676,966 | A | 4/1954 | Cusic et al. |
| 2,930,798 | A | 3/1960 | Josef et al. |
| 3,836,587 | A | 9/1974 | Grayson et al. |
| 6,440,961 | B1 | 8/2002 | Lohray et al. |
| 6,933,313 | B2 | 8/2005 | Harper et al. |
| 8,053,436 | B1 | 11/2011 | Halazy et al. |
| 8,362,277 | B2 | 1/2013 | McKnight et al. |
| 8,604,074 | B2 | 12/2013 | McKnight et al. |
| 9,095,572 | B2 | 8/2015 | McKnight et al. |
| 9,447,040 | B2 | 9/2016 | Ben-Sasson et al. |
| 10,632,102 | B2 | 4/2020 | Ben-Sasson |
| 11,191,748 | B2 | 12/2021 | Ben-Sasson |
| 2009/0317372 | A1 | 12/2009 | Kiss |
| 2011/0015217 | A1 | 1/2011 | Mcknight et al. |
| 2012/0022096 | A1 | 1/2012 | McKnight et al. |
| 2014/0329877 | A1* | 11/2014 | Ben-Sasson ............. A61P 3/10 548/444 |
| 2022/0323411 | A1 | 10/2022 | Bloomenfeld et al. |
| 2023/0089484 | A1 | 3/2023 | Balugrund et al. |
| 2023/0355584 | A1 | 11/2023 | Blaugrund et al. |

FOREIGN PATENT DOCUMENTS

| | | |
|---|---|---|
| EP | 0839806 A1 | 5/1998 |
| FR | 1186832 A | 9/1959 |
| GB | 832568 A | 4/1960 |
| WO | WO-9634863 A1 | 11/1996 |
| WO | WO-0129028 A1 | 4/2001 |
| WO | WO-0132176 A1 | 5/2001 |
| WO | WO-02060867 A2 | 8/2002 |
| WO | WO-03027084 A1 | 4/2003 |
| WO | WO-2004101579 A2 | 11/2004 |
| WO | WO-2007079239 A2 | 7/2007 |
| WO | WO-2008101406 A1 | 8/2008 |
| WO | WO-2010042445 A1 | 4/2010 |
| WO | WO-2010081115 A1 | 7/2010 |
| WO | WO-2013072915 A1 | 5/2013 |
| WO | WO-2015061280 A1 | 4/2015 |
| WO | WO-2016020919 A1 | 2/2016 |
| WO | WO-2016203468 A1 | 12/2016 |
| WO | WO-2021048626 A1 | 3/2021 |
| WO | WO-2021152390 A1 | 8/2021 |
| WO | WO-2022058792 A1 | 3/2022 |
| WO | WO-2022058795 A1 | 3/2022 |
| WO | WO-2022234337 A2 | 11/2022 |

OTHER PUBLICATIONS

Registration Certificate for TWEEN, Reg. No. 2,885,675 (U.S. Appl. No. 76/451,302). (Year: 2004).*
Akyuz et al., Successful treatment with interferon alfa in infiltrating angiolipoma: a case presenting with Kasabach-Merritt syndrome. Arch. Dis. Child. 88(1):67-68 (2003).
Berge et al. Pharmaceutical Salts. Journal of Pharmaceutical Sciences 66(1):1-19 (Jan. 1977).
Boucher. New concepts of the pathogenesis of cystic fibrosis lung disease. Eur. Respir. J. 23:146-158 (2004).
Caruso et al., Carbazole derivatives: a promising scenario for breast cancer treatment. Mini Rev Med Chem. 16(8):630-643 (2016).
Chigwada et al. Polystyrene nanocomposites based on carbazole-containing surfactants. Thermochimica Acta 436(1-2):113-121 (2005).
Divoux et al. Fibrosis in human adipose tissue: composition, distribution, and link with lipid metabolism and fat mass loss. Diabetes 59:2817-2825 (Nov. 2010).
Endo International. Endo Announces Positive Results from Phase 3 Studies of Collagenase Clostridium Histolyticum (CCH) in Patients with Cellulite. Available at www.prnewswire.com/news-releases/endo-announces-positive-results-from-phase-3-studies-of-collagenase-clostridium-histolyticum-cch-in-patients-with-cellulite-300745339.html (Nov. 7, 2018).

(Continued)

*Primary Examiner* — Theodore R. Howell
(74) *Attorney, Agent, or Firm* — WILSON SONSINI GOODRICH & ROSATI

(57) ABSTRACT

The invention provides carbazole derivatives for the treatment of fibrotic diseases (pathological collagen deposition) in tissues and organs, and related symptoms, and conditions thereof.

10 Claims, 8 Drawing Sheets

(56) References Cited

OTHER PUBLICATIONS

EP12850186.3 European Search Report dated Jun. 26, 2015.
Farmer. Molecular determinants of brown adipocyte formation and function. Gene & Development 22:1275-1269 (2008).
Friedman et al. Therapy for Fibrotic Diseases: Nearing the Starting Line. Science Translational Medicine 5(167):167 (2013).
Grivas et al., Forefoot plantar multilobular noninfiltrating angiolipoma: a case report and review of the literature. World J Surg Oncol. 6:11 (2008).
Hu et al., Synthesis and structure-activity relationships of carbazole sulfonamides as a novel class of antimitotic agents against solid tumors. Journal of Medicinal Chemistry 49(21):6273-6282 (2006).
Hung et al. Role of lung pericytes. and resident fibroblasts in the pathogenesis of pulmonary fibrosis. Am J Respir Crit Care Med 188(7):820-830 (2013).
Kawanishi et al. Coulombic effect on photoinduced electron-transfer reactions between phenothiazines and viologens. J Phys Chem 90(11):2469-2475 (1986).
Kawanishi et al. Unexpected salt effects on charge separation yields in phenothiazine derivatives-methylviologen systems. J. Phys. Chem 90:6034-6037 (1986).
King et al. A phase 3 trial of pirfenidone in patients with idiopathic pulmonary fibrosis. N Engl J Med. 370(22):2083-2092 (2014).
Lee et al. Caveolin-1 regulates chemokine. receptor 5-mediated contribution of bone marrow-derived cells to dermal fibrosis. Front Pharmacol 5:140 (2014).
Lipoma Elimination—A single RZL-012 administration can almost eliminate a large lipoma. Raziel Therapeutics Poster Apr. 2019.
Liu et al., Synthesis and antitumor activity of novel N-substituted carbazole imidazolium salt derivatives. Scientific Reports 5:13101 [1-20] (2015).
Mcmurray et al. Angiotensin-neprilysin inhibition versus enalapril in heart failure. N Engl J Med. 371(10):993-1004 (2014).
NCT03171415. Evaluation of Safety, Efficacy and Thermogenesis-induction of RZL-012 in Overweight and Obese Volunteers. Last update posted Aug. 21, 2019.
NCT03492840. Evaluation of Safety and Efficacy of RZL-012 for the Treatment of Lipedema or of Nodular Dercum's Disease. Last update posted May 14, 2019.
NCT04076891. Treatment of Women With Lipedema Involving Substantial Fat Above the Knee or of Women and Men With Nodular Dercum's Disease. Last update posted Sep. 6, 2019.
NCT04086823. A Single Blind, Randomized, Placebo-controlled, Phase 2a, 2-cohort Study for the Evaluation of Safety and Efficacy of RZL-012 for Submental Fat Reduction in Healthy Volunteers. Last updated posted Sep. 17, 2020.
NCT04229030. RZL-012 for Dercum's Disease Lipomas. Last update posted Feb. 26, 2021.
NCT04867434. Efficacy and Safety of RZL-012 on Submental Fat Reduction. Last update posted Jan. 19, 2022.
Ohno et al. PPARγ agonists induce a white-to-brown fat conversion through stabilization of PRDM16 protein. Cell Metabolism 15:395-404 (2012).
PCT/IB2020/000745 International Search Report and Written Opinion dated Jan. 26, 2021.
PCT/IB2021/000035 International Search Report and Written Opinion dated Mar. 24, 2021.
PCT/IB2021/000629 International Search Report and Written Opinion dated Nov. 15, 2021.
PCT/IB2021/000640 International Search Report and Written Opinion dated Nov. 16, 2021.
PCT/IL2012/050461 International Search Report and Written Opinion dated Apr. 2, 2013.
PCT/IL2016/050624 International Search Report and Written Opinion dated Sep. 23, 2016.
Petrovic et al. Chronic peroxisome proliferator-activated receptor gamma (PPARgamma) activation of epididymally derived white adipocyte cultures reveals a population of thermogenically competent, UCP1-containing adipocytes molecularly distinct from classic brown adipocytes. J Biol Chem 258(10):7153-7164 (2010).
Quinton et al. Cystic fibrosis: a disease in electrolyte transport. FASEB 4:2709-2717 (Jul. 1990).
Richeldi et al. Investigators. Efficacy and safety of nintedanib in idiopathic pulmonary fibrosis. N Engl J. Med. 370(22):2071-2082 (2014).
Saxe. Your brain on drugs. Nature American. 6:639-640 (2010).
Talathi et al., Fat busters: lipolysis for face and neck. J Cutan Aesthet Surg. 11(2):67-72 (2018).
Tsutsumi et al., Carbazole scaffold in medicinal chemistry and natural products: a review from 2010-2015. Current Topics in Medicinal Chemistry 16(11):1290-1313 (2016).
U.S. Appl. No. 14/358,431 Office Action dated Aug. 31, 2015.
U.S. Appl. No. 14/358,431 Office Action dated Feb. 2, 2015.
U.S. Appl. No. 15/736,307 Office Action dated Aug. 6, 2018.
U.S. Appl. No. 15/736,307 Office Action dated Nov. 23, 2018.
U.S. Appl. No. 16/826,632 Office Action dated Mar. 26, 2021.
Winbury et al. Autonomic blocking compounds. III. The ganglion blocking and parasympatholytic actions of a series of quaternary ammonium derivatives containing the phenothiazine nucleus. J Pharmacol Exp Ther 111:395-403 (1954).
WYNN. Cellular and molecular mechanisms of fibrosis. J. Pathol. 214:199-210 (2008).
Saturnino et al. Inhibition of Human Topoisomerase II by N,N,N-Trimethylethanammonium Iodide Alkylcarbazole Derivatives. ChemMedChem 13(24):2635-2643 (2018).
Eliason et al. Adiposis Dolorosa Pain Management. Fed Pract. 36(11):529-533 (2019).
Gueta et al. RZL-012, a New Fat Dissolving Molecule, Tested in Dercum's Disease Patients. Dermatol Surg 47(8):1165-1166 (2021).
PCT/IB2022/000437 International Search Report and Written Opinion dated Jan. 12, 2023.

\* cited by examiner

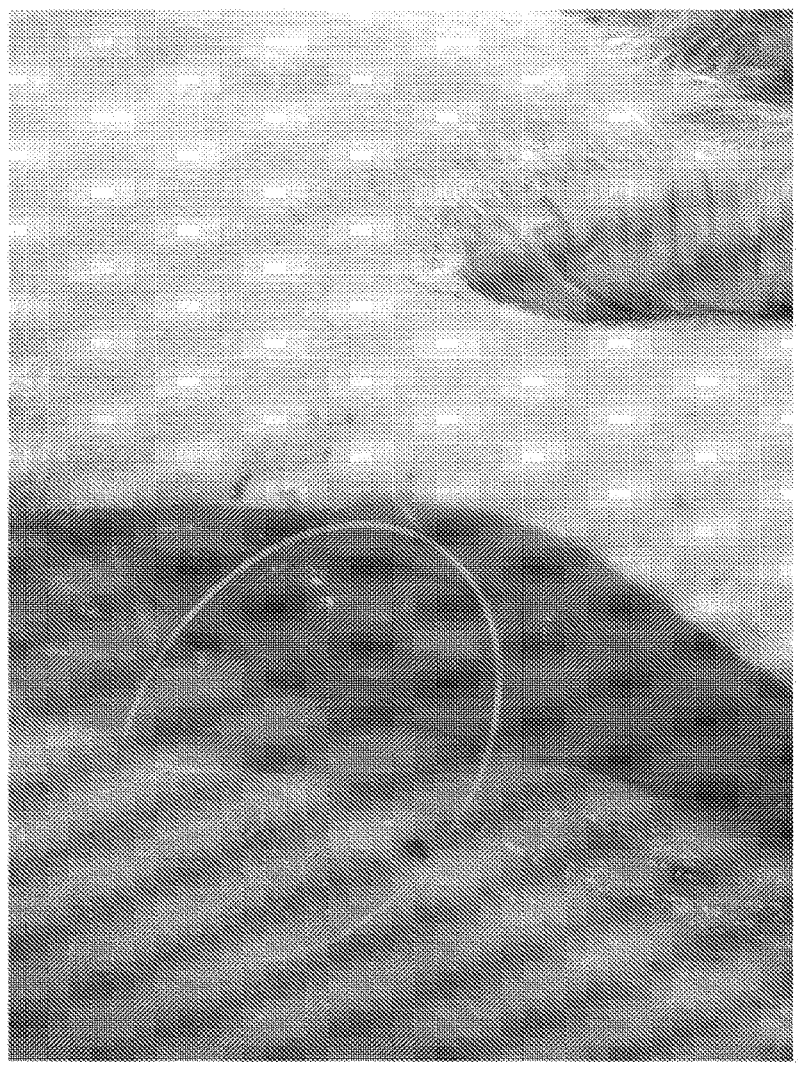
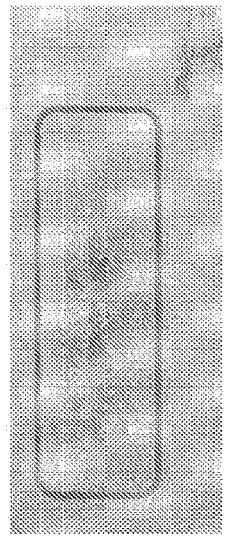
Fig. 1B
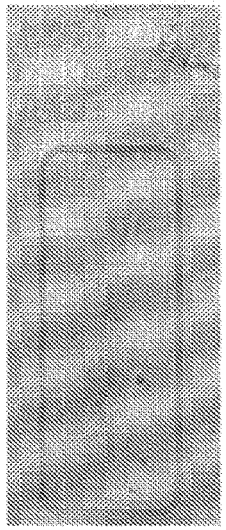
Fig. 1C
Fig. 1A

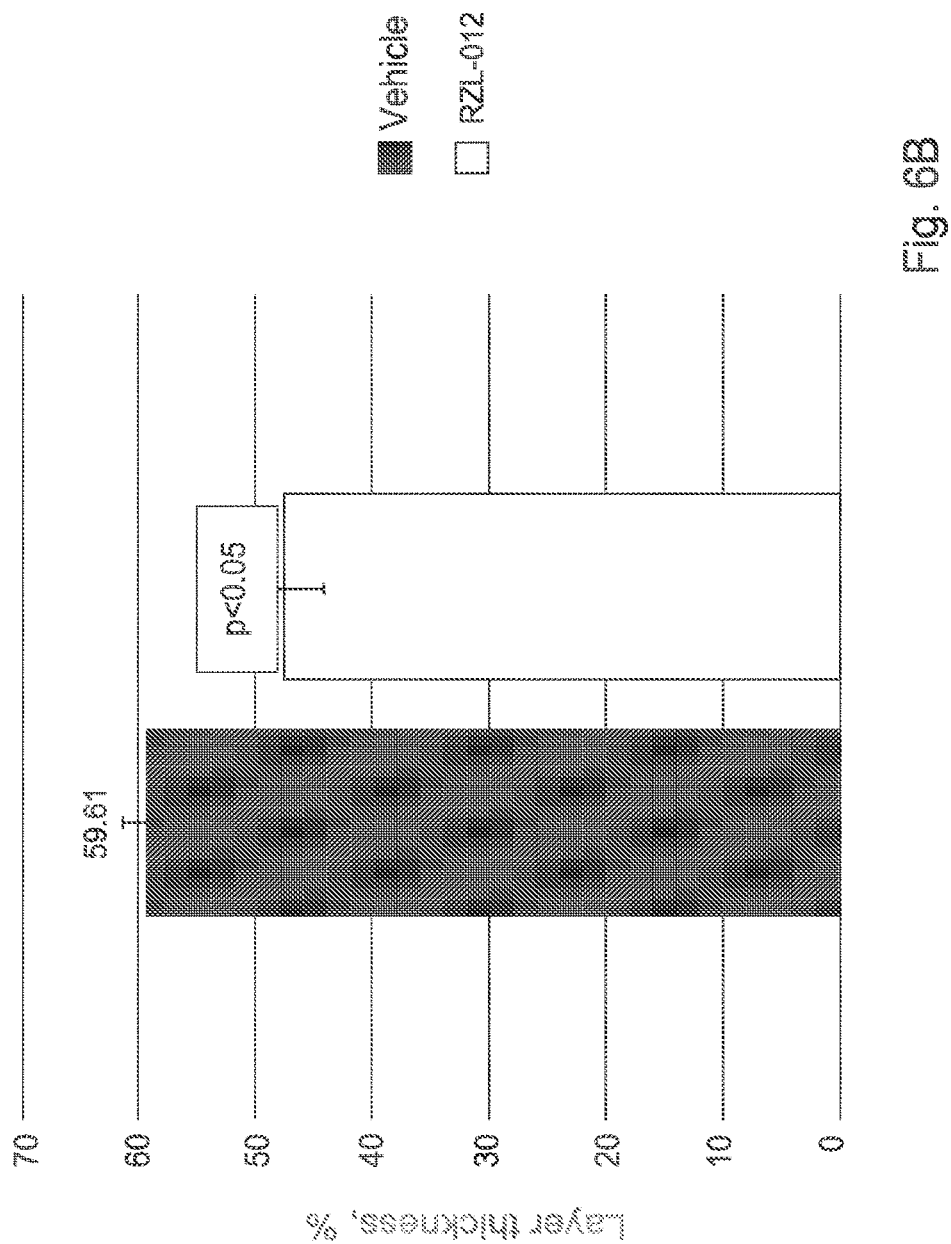

CARBAZOLE DERIVATIVES FOR THE TREATMENT OF FIBROTIC DISEASES AND RELATED SYMPTOMS, AND CONDITIONS THEREOF

CROSS-REFERENCE TO RELATED APPLICATIONS

This application is a continuation of U.S. patent application Ser. No. 16/826,632, filed Mar. 23, 2020, which is a divisional application of U.S. patent application Ser. No. 15/736,307 filed Dec. 14, 2017, now U.S. Pat. No. 10,632,102 issued Apr. 28, 2020, which is a U.S. National Phase Application of PCT International Application No. PCT/IL2016/050624, International Filing Date Jun. 14, 2016, claiming priority of U.S. Provisional Patent Application No. 62/175,552, filed Jun. 15, 2015, each of which are hereby incorporated by reference.

TECHNOLOGICAL FIELD

The present invention provides carbazole derivatives for the treatment of fibrotic diseases (pathological collagen deposition) in essential tissues and organs, and related symptoms, and conditions thereof.

BACKGROUND ART

1. Wynn T A. Cellular and molecular mechanisms of fibrosis. J Pathol. 2008; 214:199-210.
2. King T E, et al, for the ASCEND Study Group. A phase 3 trial of pirfenidone in patients with idiopathic pulmonary fibrosis. N Engl J Med. 2014 May 29; 370(22):2083-2092
3. Richeldi L, et al, for the INPULSIS Trial Investigators. Efficacy and safety of nintedanib in idiopathic pulmonary fibrosis. N Engl J Med. 2014 May 29; 370(22):2071-2082.
4. McMurray J J, Packer M, Desai A S, Gong J, Lefkowitz M P, Rizkala A R, Rouleau J L, Shi V C, Solomon S D, Swedberg K, Zile M R; for the PARADIGM-HF Investigators and Committees. Angiotensin-neprilysin inhibition versus enalapril in heart failure. N Engl J Med. 2014, Sep 11; 371(11):993-1004.
5. Hung C, Linn G, Chow Y H, Kobayashi A, Mittelsteadt K, Altemeier W A, Gharib S A, Schnapp L M, Duffield J S. Role of lung pericytes and resident fibroblasts in the pathogenesis of pulmonary fibrosis. Am J Respir Crit Care Med. 2013 Oct. 1; 188(7):820-830.
6. Lee R, Perry B, Heywood J, Reese C, Bonner M, Hartfield C M, Silver R M, Visconti R P, Hoffman S, Tourkina E. Caveolin-1 regulates chemokine receptor 5-mediated contribution of bone marrow-derived cells to dermal fibrosis. Front Pharmacol Jun. 11, 2014; 5:140.
7. Friedman S. L., Sheppard D., Duffield J. S., Violette S. Therapy for Fibrotic Diseases: Nearing the Starting Line. Science Translational Medicine, 2013; 5 (167): 167.

BACKGROUND

It has been estimated that 45% of all deaths in developed countries are due to organ dysfunction resulting from fibrosis (Wynn T A et al). It is implicated in diseases such as cardiovascular disease, pulmonary fibrosis, liver cirrhosis, and chronic kidney failure. Virtually every organ in the body is vulnerable; the affected organ shrinks, hardens, and ceases to function properly.

Cellular and Molecular Mechanisms Underlying Fibrosis

Fibrosis is not a disease; it is a pathology. As such, it runs orthogonally to many different therapeutic indications and cross multiple organs. The list of fibrosis related maladies include end-stage diseases such as: Liver cirrhosis, Kidney fibrosis, Lung-fibrosis, Heart failure, Bone-marrow (myelofibrosis), and some also connect fibrosis with aspects of Alzheimer's Disease.

Fibrosis can also be a part of the following conditions: Adhesion-formation following abdominal surgery, Organ fibrosis of irradiation-damaged tissues, Over-reacting dermal scars (keloids). It was further shown that activated myofibroblasts play a detrimental role in tumor progression. Tumors like breast cancer and pancreatic cancer are especially rich in those cells that in this context are known as "cancer-associated fibroblasts" (CAF).

Pathophysiology

The common denominator of all fibrosis-related diseases is the transformation of an otherwise placid fibroblast into a "hyper-active" myofibroblast. The myofibroblast is the cell in charge of orchestrating wound repair. In response to injury, it cranks up its metabolic activity, proliferates rapidly, secrets collagen and other extracellular-matrix components, and develops muscle-like contractile properties to physically close wounds. In an acute injury, like a cut or a burn, once its work done, the myofibroblast return to quiescence and reassumes its quiet life as a resident tissue fibroblast. But in injury that is chronic and lifelong, myofibroblasts persist and eventually take over, filling the organ with collagen, laying down scar tissue, crowding out and eventually destroying the functional tissue in the organ. With time, the organ can no longer function properly; it fails.

After injury, organs in the body undergo a wound-healing response, intended to create new connective tissue. This process involves a wide variety of cells, molecules, and signaling pathways. Critical cells in the process are the fibroblasts and the smooth muscle-like myofibroblasts into which they differentiate which both produce extracellular matrix (ECM) and govern its resorption. Pericytes, which typically form a sheath around blood vessels and regulate vascular stability, are another group of fibrogenic cells, which are major contributors to the myofibroblast population in a mouse model of pulmonary fibrosis (Hung C et al). Finally, epithelial-mesenchymal transition (EMT), in which epithelial cells differentiate into mesenchymal cells, is thought to create an environment conducive to fibrosis, however, the contribution of EMT to collagen synthesis remains debated.

In pathological fibrosis, the balance is lost between normal production of ECM (scar tissue) and its resorption. With progressive fibrosis, the tissue becomes less elastic and pliable and more fibrous, stringy, and tough. These changes in tissue architecture alter organ function and can ultimately lead to organ failure. Pathological fibrosis in any organ system involves more than one of these myofibroblast precursors, suggesting that combination regimens of anti-fibrotic agents, each targeting a different precursor, might be necessary for successful therapy.

State of the Art Treatments of Fibrosis

Despite the overwhelming need, few agents with anti-fibrotic effects have made it to the market, leaving millions of patients with very limited treatment options. Clinical trials of anti-fibrotic therapies reported beneficial results for idiopathic pulmonary fibrosis (King T E, et al; Richeldi L, et al) and heart failure (McMurray J J et al).

One of the most promising treatments focus on blocking a pathway driven by a molecule known as TGF-β, which is as a central mediator of fibrosis. One approach developed by Genzyme, Eli Lilly, and Biogen Idec, includes a variety of humanized antibodies against TGF-β. However, there have been concerns that inhibiting this pathway could also impair the healthy process of tumor suppression. Another strategy, developed by Gilead Sciences is using antibodies to block an enzyme that promotes cross-links among proteins in scar tissue. Such cross-linking is thought to stiffen the scar and hamper normal tissue repair and scar resolution. A third approach, explored by Genentech, Novartis, MedImmune and Sanofi, targets cytokines, or messenger chemicals, IL-4 and IL-13, which regulate fibrosis in several animal models. Hoffman and Tourkina are inventors on an issued U.S. patent for the use of caveolin-1 scaffolding domain (CSD) as an anti-fibrotic treatment in mice model of Scleroderma, in which CSD substitutes for the lost caveolin-1 and prevents fibrosis (Lee R et al). New anti-fibrosis agents tested in Idiopathic Pulmonary Fibrosis such as pirfenidone and nintedanib slowed a decline in fibrosis however, they have not reversed the disease (King T E et al).

The Unmet Need for a Treatment of Fibrosis

As the mechanisms underlying fibrosis are becoming better elucidated and as more and more biomarkers of disease are being identified, the interest in developing anti-fibrotic agents has been growing. Efforts should be made to better target anti-fibrotic therapies by developing biomarkers that will predict which patients might benefit from a particular therapy.

Scleroderma, the prototype of the fibrotic disease, is characterized by deposition of excessive collagen in the skin of the face, extremities, and trunk as well as injury to the capillaries. If an anti-fibrotic agent is demonstrated to be efficacious in scleroderma, that could mean that it holds promise for treating the fibrotic diseases of the lung, heart, liver, kidneys and other organs (Friedman S L et al). In other words, from a pathophysiology point of view, all the above diseases represents a single entity; you cure one, you cure them all.

GENERAL DESCRIPTION

The inventors of the present application have found that compositions comprising at least one active agent having the general formula (I) or any salt thereof, are suitable in uses and methods of treating of conditions or diseases associated with excessive collagen deposition:

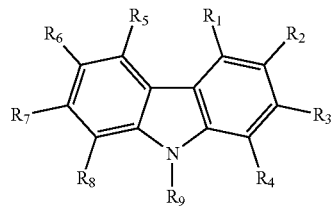

(I)

Wherein each of $R_1$-$R_8$ is independently selected from the group consisting of H, OH, SH, halogen, nitro, amino, nitrilo, nitroso, acetyl, acetamido, acylamido, alkylamino, straight or branched $C_1$-$C_5$ alkyl, straight or branched $C_1$-$C_5$alkenyl, straight or branched $C_1$-$C_5$alkynyl, amine, straight or branched $C_1$-$C_5$alkoxy, straight or branched $C_1$-$C_5$ carboxyl, straight or branched $C_1$-$C_5$ ester, straight or branched $C_1$-$C_5$ thioxy, straight or branched $C_1$-$C_5$ sulfinyl, straight or branched $C_1$-$C_5$ thionyl; $R_9$ is selected from straight or branched $C_1$-$C_9$ alkyl, straight or branched $C_1$-$C_9$alkenyl, straight or branched $C_1$-$C_9$alkynyl, piperazinyl, pyridinyl, piperidinyl, morpholinyl and thiomorpholinyl; $R_9$ is substituted with at least one quaternary amino (ammonium) group or a phophonium group.

Such compositions were also found to be of use in the treatment of conditions or diseases associated with myofibroblasts activation.

The term "myofibroblasts activation" encompasses any physiological process wherein myofibroblast became metabolically activated. In this process myofibroblast (a smooth muscle-like fibroblast) is transformed from dormant stage to active metabolic stage. The activation of this process is typically due to a response to injury, the activated cells proliferate, secret collagen and other extracellular-matrix components, and develop muscle-like contractile properties required to close wounds. In diseases or conditions associated with fibrosis, myofibroblasts persist, filling the organ with collagen, and eventually destroying the functional tissue of the organ.

When referring to "conditions or diseases associated with excessive collagen deposition" it should be understood to include any conditions or diseases that are directly or indirectly related to myofibroblasts activation leading to irreversible excessive collagen deposition in an organ or a tissue of a subject.

Without being bound by theory, the inventors have found that composition disclosed herein behave as a chemo-attractant of fibrocytes/fibroblasts, causing them to transfer from vital organs via the blood stream to the injection site where the composition has been administered. This mechanism leads to sparing the vital organs from development of fibrosis. Thus, the compound of general formula (I) is an anti-fibrotic agent that can be used for treatment of the fibrotic diseases of the lung, heart, liver, kidneys and other vital organs.

Without being bound by theory, it is postulated that bone-marrow derived circulating fibrocytes serve as precursor cells that home to the site where the carbazole derivative of the invention was injected and differentiate there to myofibroblasts. Thus, by attracting them to the "neutral territory" of s.c. fat, they are no longer available to vital organs, namely, myofibroblast trap. In addition, it could also be postulated that several factors (such as for example TGF-β3, Pentraxin2 and IL-10) might be secreted during local fibrosis at the site where the carbazole derivative of the invention was injected, and thereby inhibiting systemic fibrosis.

In some embodiments, at least one of $R_1$-$R_8$ is independently selected from the group consisting of OH, SH, halogen, nitro, amino, nitrilo, nitroso, acetyl, acetamido, acylamido, alkylamino, straight or branched $C_1$-$C_5$ alkyl, straight or branched $C_1$-$C_5$alkenyl, straight or branched $C_1$-$C_5$alkynyl, amine, straight or branched $C_1$-$C_5$alkoxy, straight or branched $C_1$-$C_5$ carboxyl, straight or branched $C_1$-$C_5$ ester, straight or branched $C_1$-$C_5$ thioxy, straight or branched $C_1$-$C_5$ sulfinyl, straight or branched $C_1$-$C_5$ thionyl.

In other embodiments, at least one of $R_1$, $R_2$, $R_3$, $R_5$, $R_6$, $R_7$ is independently selected from the group consisting of OH, SH, halogen, nitro, amino, nitrilo, nitroso, acetyl, acetamido, acylamido, alkylamino, straight or branched $C_1$-$C_5$ alkyl, straight or branched $C_1$-$C_5$alkenyl, straight or branched $C_1$-$C_5$alkynyl, amine, straight or branched $C_1$-$C_5$alkoxy, straight or branched $C_1$-$C_5$ carboxyl, straight or branched $C_1$-$C_5$ ester, straight or branched $C_1$-$C_5$ thioxy, straight or branched $C_1$-$C_5$ sulfinyl, straight or branched $C_1$-$C_5$ thionyl.

In some embodiments, at least one of $R_1$-$R_8$ is different than H. In other embodiments, at least two of $R_1$-$R_8$ is different than H. In further embodiments, at least three of $R_1$-$R_8$ is different than H. In further embodiments, at least four of $R_1$-$R_8$ is different than H.

In some embodiments at least one of $R_1$-$R_4$ is a halogen or at least one of $R_5$-$R_8$ is a halogen. In some embodiments at least two of $R_1$-$R_4$ are independently a halogen or at least two of $R_5$-$R_8$ are independently a halogen. In another embodiment at least two of $R_1$-$R_8$ are independently a halogen. In further embodiments, said halogen is Br.

In some embodiments, at least one of $R_1$-$R_4$ is OH. In further embodiments, at least one of $R_5$-$R_9$ is OH. In some embodiments at least two of $R_1$-$R_4$ are independently OH or at least two of $R_5$-$R_8$ are independently OH. In another embodiment at least two of $R_1$-$R_8$ are independently OH.

In some embodiments at least one of $R_1$-$R_4$ is a nitro or at least one of $R_5$-$R_8$ is a nitro. In some embodiments at least two of $R_1$-$R_4$ are independently a nitro or at least two of $R_5$-$R_8$ are independently a nitro. In another embodiment at least two of $R_1$-$R_8$ are independently a nitro. In further embodiments, at least one of $R_1$-$R_4$ is a nitro and at least one of $R_5$-$R_8$ is a nitro.

In some embodiments, $R_9$ is selected from straight or branched $C_1$-$C_9$ alkyl, straight or branched $C_1$-$C_9$alkenyl, straight or branched $C_1$-$C_9$alkynyl, piperazinyl, pyridinyl, piperidinyl, morpholinyl and thiomorpholinyl, and further $R_9$ is substituted (at any position of the substituent defined above) by at least one quaternary amino (ammonium) group.

In some other embodiments, $R_9$ is selected from straight or branched $C_1$-$C_9$ alkyl, straight or branched $C_1$-$C_9$alkenyl, straight or branched $C_1$-$C_9$alkynyl, piperazinyl, pyridinyl, piperidinyl, morpholinyl and thiomorpholinyl, and further $R_9$ is substituted (at any position of the substituent defined above) by at least one a phophonium group.

In some embodiments, $R_9$ is a straight or branched $C_1$-$C_9$ alkyl substituted with at least one quaternary amino group.

In another embodiment, said at least one quaternary amino group has a general formula (V):

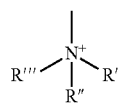

(V)

Wherein each of R', R" and R'" is independently selected from a group consisting of straight or branched $C_1$-$C_9$ alkyl, straight or branched $C_1$-$C_9$ alkenyl and straight or branched $C_1$-$C_9$ alkynyl.

In yet another embodiment, each of R', R" and R'" is independently a straight or branched $C_1$-$C_9$ alkyl.

In some embodiments a composition according to the invention comprises at least one active agent selected from:

3-(3,6-dibromo-9H-carbazol-9-yl)-N,N,N-trimethylpropan-1-aminium

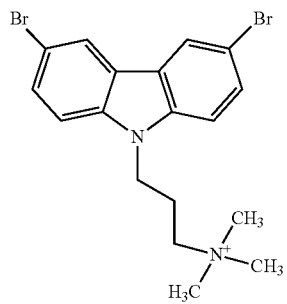

5-(9H-carbazol-9-yl)-N,N,N-trimethylpentan-1-aminium

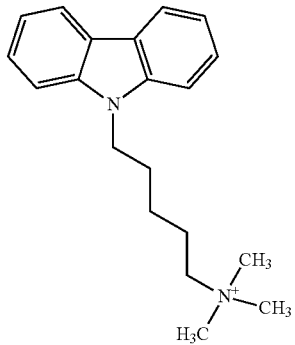 [SMILES: C[N+](C)(C)CCCCCn1c2ccccc2c2ccccc21]

5-(2-hydroxy-9H-carbazol-9-yl)-N,N,N-trimethylpentan-1-aminium

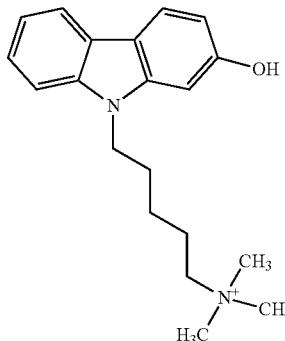

5-(3,6-dibromo-9H-carbazol-9-yl)-N,N,N-trimethylpentan-1-aminium

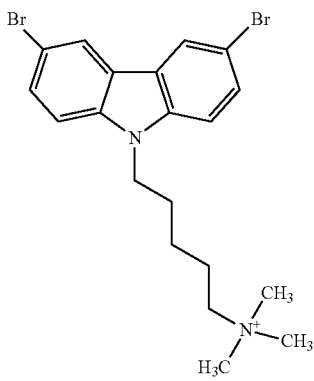 [SMILES: C[N+](C)(C)CCCCCn1c2ccc(Br)cc2c2cc(Br)ccc21]

or any salt thereof.

The term "halogen" is meant to encompass any halogen moiety selected from F, Cl, Br and I.

The term "nitro" is a —$NO_2$ moiety.

The term "amino" refers to —$NH_2$, —NHR, —NRR', wherein R, R' and R" are each independently selected from straight or branched $C_1$-$C_{10}$ alkyl (also termed "alkylamino"), straight or branched $C_2$-$C_{10}$ alkenyl, straight or branched $C_2$-$C_{10}$ alkynyl. The term amino also includes quaternary ammonium moiety of the form—$^+$NRR'R" wherein R, R' and R" are as defined herein above.

The term "nitrilo" refers to —CN,

The term "nitroso" refers to a NO moiety, including C-nitroso moieties (e.g., nitrosoalkanes —R—N═O, wherein R is selected from straight or branched $C_1$-$C_{10}$ alkanyl, straight or branched $C_2$-$C_{10}$ alkenylene, straight or branched $C_2$-$C_{10}$ alkynylene), S-nitroso moieties (nitrosothiols; —S—N═O or —RS—N═O wherein R is selected from straight or branched $C_1$-$C_{10}$ alkanyl, straight or branched $C_2$-$C_{10}$ alkenylene, straight or branched $C_2$-$C_{10}$ alkynylene), N-nitroso moieties (e.g., nitrosamines; —N═N═O, RN—N═O, —RR'N—N═O), and O-nitroso moieties (—O—N═O, —RO—N═O wherein R is selected from straight or branched $C_1$-$C_{10}$ alkanyl, straight or branched $C_2$-$C_{10}$ alkenylene, straight or branched $C_2$-$C_{10}$ alkynylene).

The term "acetyl" refers to a —C(═O)$CH_3$ moiety.

The terms "acetamido" and "acylamido" refers to —$CH_2$C(═O)$NH_2$ and $CH_3$C(═O)NH— respectively.

The term "straight or branched $C_1$-$C_5$ alkyl" and "straight or branched $C_1$-$C_9$ alkyl" encompasses a saturated hydrocarbon chain having between 1 to 5 or 1 to 9 carbon atoms.

The term "straight or branched $C_1$-$C_5$ alkenyl" and "straight or branched $C_2$-$C_9$ alkenyl" encompasses a hydrocarbon chain having between 1 to 5 or 1 to 9 carbon atoms and at least one double bond.

The term "straight or branched $C_2$-$C_5$ alkynyl" and "straight or branched $C_2$-$C_9$ alkynyl" encompasses a hydrocarbon chain having between 1 to 5 or 1 to 9 carbon atoms and at least one triple bond.

The term "straight or branched $C_1$-$C_5$ alkoxy" is meant to encompass an —OR moiety wherein R is selected from a straight or branched $C_1$-$C_5$ alkyl, straight or branched $C_2$-$C_5$ alkenyl and straight or branched $C_2$-$C_5$alkynyl.

The term "straight or branched $C_1$-$C_5$ carboxyl" refers to a —R—C(═O)OH moiety wherein R is selected from a straight or branched $C_1$-$C_5$ alkanyl, straight or branched $C_2$-$C_5$ alkenylene and straight or branched $C_2$-$C_5$ alkynylene.

The term "straight or branched $C_1$-$C_5$ ester" refers to a RC(═O)O— moiety wherein R is selected from a straight or branched $C_1$-$C_5$ alkyl, straight or branched $C_2$-$C_5$ alkenyl and straight or branched $C_2$-$C_5$ alkynyl.

The term "straight or branched $C_1$-$C_5$ thioxy" refers to a RS— moiety wherein R is selected from a straight or branched $C_1$-$C_5$ alkyl, straight or branched $C_2$-$C_5$ alkenyl and straight or branched $C_2$-$C_5$ alkynyl.

The term "straight or branched $C_1$-$C_5$ sulfinyl" and "straight or branched $C_1$-$C_5$ thionyl" refers to a RS(═O)— moiety wherein R is selected from a straight or branched $C_1$-$C_5$ alkyl, straight or branched $C_2$-$C_5$ alkenyl and straight or branched $C_2$-$C_5$ alkynyl.

The term "phosphonium" refers to a —$P^+$RR'R" moiety wherein R, R' and R" are each selected from a straight or branched $C_1$-$C_{10}$ alkyl, straight or branched $C_2$-$C_{10}$ alkenyl and straight or branched $C_2$-$C_{10}$ alkynyl.

The term "piperazinyl" encompasses a moiety selected from:

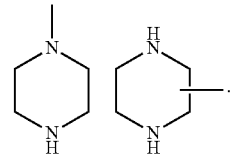

The term "pyridinyl" encompasses a moiety:

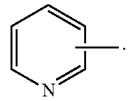

The term "piperidinyl" encompasses a moiety selected from:

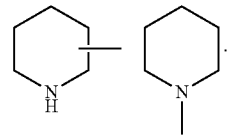

The term "morpholinyl" encompasses a moiety selected from:

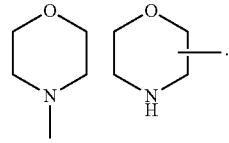

The term "thiomorpholinyl" encompasses a moiety selected from:

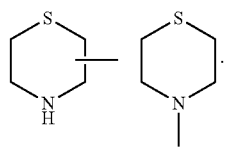

The compounds of the present invention, as defined above, may have the ability to crystallize in more than one form, a characteristic, which is known as polymorphism, and it is understood that such polymorphic forms ("polymorphs") are within the scope of formulae (I). Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers or as two or more diastereomers. Accordingly, the compounds of this invention include mixtures of enantiomers as well as purified enantiomers or enantiomerically enriched mixtures. Furthermore, the compounds of this invention include mixtures of diastereomers, as well as purified stereoisomers or diastereomerically enriched mixtures. Also included within the scope of the invention are the individual isomers of the compounds of the invention, as defined above, as well as any wholly or partially mixtures thereof. The present invention also covers the individual isomers of the compounds represented by the formulas above as mixtures with isomers thereof in which one or more chiral centers are inverted.

It is also noted that the compounds of the present invention may form tautomers. It is understood that all tautomers and mixtures of tautomers of the compounds of the present invention, are included within the scope of the compounds of the present invention.

In some embodiments, said composition is a pharmaceutical composition, wherein said salt is a pharmaceutically acceptable salt.

Pharmaceutical compositions of the invention may additionally comprise any other suitable substances such as other therapeutically useful substances, diagnostically useful substances, pharmaceutically acceptable carriers or the like.

In some embodiments a compound or composition of the invention is administered (suitable to be administered) into an adipose tissue of a subject. In some embodiments said compound or composition of the invention is administered directly into an adipose tissue of a subject. In other embodiments said administration is via injection. In other embodiments, said administration is a transdermal administration. Under such embodiments, transdermal admonition can be achieved by any transdermal formulation known in the art and/or via a transdermal delivery device (for example a patch containing a compound or composition of the invention) at a close proximity to the adipose tissue location of said subject (for example the direct skin or mucosal tissue in contact with said adipose tissue).

Pharmaceutical compositions of the invention comprise a compound of the subject invention in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous, intra-adipose tissue and intradermal) administration or administration via an implant. The compositions may be prepared by any method well known in the art of pharmacy. Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules (including softgel capsules), or as a powder or granules, or as a solution or suspension. The active ingredient may also be presented as a bolus, liquid formulation or paste. The compositions can further be processed into a suppository or enema for rectal administration.

The invention further includes a pharmaceutical composition, as hereinbefore described, in combination with packaging material, including instructions for the use of the composition for a use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

In some embodiments, compositions of the invention include also compositions where the compound of the invention is formulated in a fat emulsion formulation (i.e. formulated in conventional formulation processes to produce an emulation comprising at least one fat component, either from a natural or synthetic source), such as for example Intralipid formulation (in any concentration).

The exact dose and regimen of administration of the composition will necessarily be dependent upon the therapeutic or nutritional effect to be achieved and may vary with the particular formula, the route of administration, and the age and condition of the individual subject to whom the composition is to be administered.

The invention also includes any salt of a compound of the invention, including any pharmaceutically acceptable salt, wherein a compound of the invention has a net charge (either positive or negative) and at least one counter ion (having a counter negative or positive charge) is added thereto to form said salt. The phrase "pharmaceutically acceptable salt(s)", as used herein, means those salts of compounds of the invention that are safe and effective for pharmaceutical use in mammals and that possess the desired biological activity. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Salts of the invention may also include a counter anion being a halogen anion such as for example chloride and bromide anions. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 *J. PHARM. SCI.* 1-19 (1977), incorporated herein by reference.

In some embodiments the composition of the invention has water content of less than 50% of total composition weight. In some other embodiments the water content of a composition of the invention is less than 30% of total composition weight. In further embodiments the water content of a composition of the invention is less than 10% of total composition weight. In further embodiments, the water content of a composition of the invention is between about 30% to about 0%, of total composition weight. In further embodiments, the water content of a composition of the invention is about 30%, 25%, 20%, 15%, 10%, 5%, 4%, 3%, 2%, 1%, 0%, of total composition weight.

In some embodiments, a composition of the invention comprises at least 0.1% by weight of said at least one active agent of total composition. In further embodiments, the composition comprises between about 0.1% to about 10% by weight of said at least one active agent of total composition. In further embodiments, the composition comprises between 0.1%, 0.5%, 1%, 2%, 3%, 4%, 5%, 6%, 7%, 8%, 9%, 10% by weight of said at least one active agent of total composition. In further embodiments, the composition comprises between about 1% to about 5% by weight of said at least one active agent of total composition. In further embodiments, the composition comprises about 1%, 1.5%, 2%, 2.5%, 3%, 3.5%, 4%, 4.5%, 5% by weight of said at least one active agent of total composition.

In some embodiments, a composition of the invention is formulated for topical application or parenteral injection (such as subcutaneous injection) to a non-essential fat tissue of said patient.

The term "non-essential fat tissue" should be understood to include any fat tissue that is not an essential part of an organ. In some embodiments, said non-essential fat tissue is abdominal subcutaneous tissue.

In some embodiments, the conditions or diseases associated with excessive collagen deposition or with myofibroblasts activation is fibrosis.

The term "fibrosis" as used herein should be understood to encompass any condition or disease that are related to directly or indirectly to a process of pathological excess of fibrous connective tissue in an organ or tissue.

Diseases or disorders associated with fibrosis are selected from: pulmonary fibrosis, cystic fibrosis, kidney fibrosis, liver cirrhosis, endomyocardial fibrosis, myocardial fibrosis, atrial fibrosis, mediastinal fibrosis, myelofibrosis, retroperitoneal fibrosis, progressive massive fibrosis, nephrogenic systemic fibrosis, Carpal tunnel syndrome, joint fibrosis, Crohn's Disease, Keloid, Scleroderma, arthrofibrosis, Peyronie's disease, Dupuytren's contracture, adhesive capsulitis and any symptom or condition associated therewith.

BRIEF DESCRIPTION OF THE DRAWINGS

FIG. 1A-1C: Macroscopic view of the scars at time of 2 months sacrifice of a pig treated with RZL-012 of the invention. FIG. 1A is a view of a cross-section cut through the middle of the scar at the non-treated side (L), no internal scar-tissue can be observed. FIG. 1B is an external view of the scar at the treated side (R). FIG. 1C shows the external view of the scar at the non-treated side (L).

FIG. 2A is a view of a cross-section cut through the middle of the scar at the non-treated side (L). White scar tissue can be clearly see along the cut (marked by a black rectangle). FIG. 2B is an external view of the scar at the treated side (R). FIG. 2C shows the external view of the scar at the non-treated side (L).

FIG. 3A shows the right side RZL-012 treated scar histology. FIG. 3B shows the left side RZL-012 treated scar histology. FIG. 3C shows the right side Kythera treated scar histology. FIG. 3D shows the left side Kythera treated scar histology. While the entire width of the scar-tissue of the RZL-012 treated pig fits into the field of this magnification (FIGS. 3A-B), the scar-tissue of the Kythera treated pig is around five times wider and cannot be contained as a whole under this microscope magnification. Therefore, only small part of it can be seen in this field (FIG. 3C-D).

FIG. 4A shows the right side RZL-012 treated scar histology. FIG. 4B shows the left side RZL-012 treated scar histology. FIG. 4C shows the right side Kythera treated scar histology. FIG. 4D shows the left side Kythera treated scar histology.

FIG. 5A shows the right side RZL-012 treated scar histology. FIG. 5B shows the left side RZL-012 treated scar histology. FIG. 5C shows the right side Kythera treated scar histology. FIG. 5D shows the left side Kythera treated scar histology.

FIG. 6A-6C: Results of Injured arteries analysis of the unilateral ureteral ligation (UUO) kidney fibrosis model of Example 2 below. FIG. 6A and FIG. 6B show the Adventitia/Muscular layers ratio (in percent) for each rat in the example (FIG. 6A) and in average (FIG. 6B). FIG. 6C shows the stained tissue sections (Masson-Trichrome) wherein the muscular layer and an outer layer, excessively rich in collagen, in the kidneys defined as "Adventitia" are visible.

DETAILED DESCRIPTION OF EMBODIMENTS

Example 1

Comparative Experiments Showing Effect of RZL-012 of the Invention and Kybella

The objective of this study is to evaluate the remote effect on local injection of RZL-012 of the invention (5-(3,6-dibromo-9H-carbazol-9-yl)-N,N,N-trimethylpentan-1-aminium) into the s.c. fat, on scar formation in pigs, compared with Kybella (an injectable formulation of Deoxycholate developed by Kythera) an agent that bluntly destroys s.c. fat.

Materials

1. Kythera preparation (according to published formulation): an aqueous solution of 5% Phosphatidylcholine, 4.75% Sodium deoxycholate and 0.9% Benzyl Alcohol.
2. RZL-012 of the invention (5-(3,6-dibromo-9H-carbazol-9-yl)-N,N,N-trimethylpentan-1-aminium) of the invention preparation: 5.0% (w/v) RZL-012 in the below indicated formulation:

| Raw Material | % (w/w) | (g/vial) |
|---|---|---|
| RZL-012 | 5.6 | 0.28 |
| Tween 80 | 10 | 0.5 |
| Propylene glycol | 57 | 2.85 |
| Benzyl alcohol | 3 | 0.15 |
| Water for Injection | 24.4 | 1.22 |
| Total per vial | 100 | 5.0 |

Note: RZL-012 powder contains also a counter ion and some bound water molecules, amounting to around 10% of the weight.

Experimental Model and Procedures

Eighty kilogram pigs were injected with either Kythera or RZL-012 of the invention preparation, into the s.c. fat (1 cm depth, 27 G needle), at 10 sites, divided into two clusters, on the right flank only. The injection at each site was of a volume of 0.5 ml. In addition, a cut through the s.c. fat was made at the midline of each pig at the right and at the left flank.

Animals were housed in the animal unit of Biotechfarm, Israel and fed on a diet weighing 2% of body weight (B.W.) per day divided to two meals, based on the last effective weekly body weighing.

After 2 months from the day of treatment, the animals were sacrificed; the scars on both sides were photographed before and after making a cross section in the middle of each scar. Thereafter, tissue samples of all cross-sections were formalin-fixed and processed for H & E histology staining.

Results

Figure 2A:
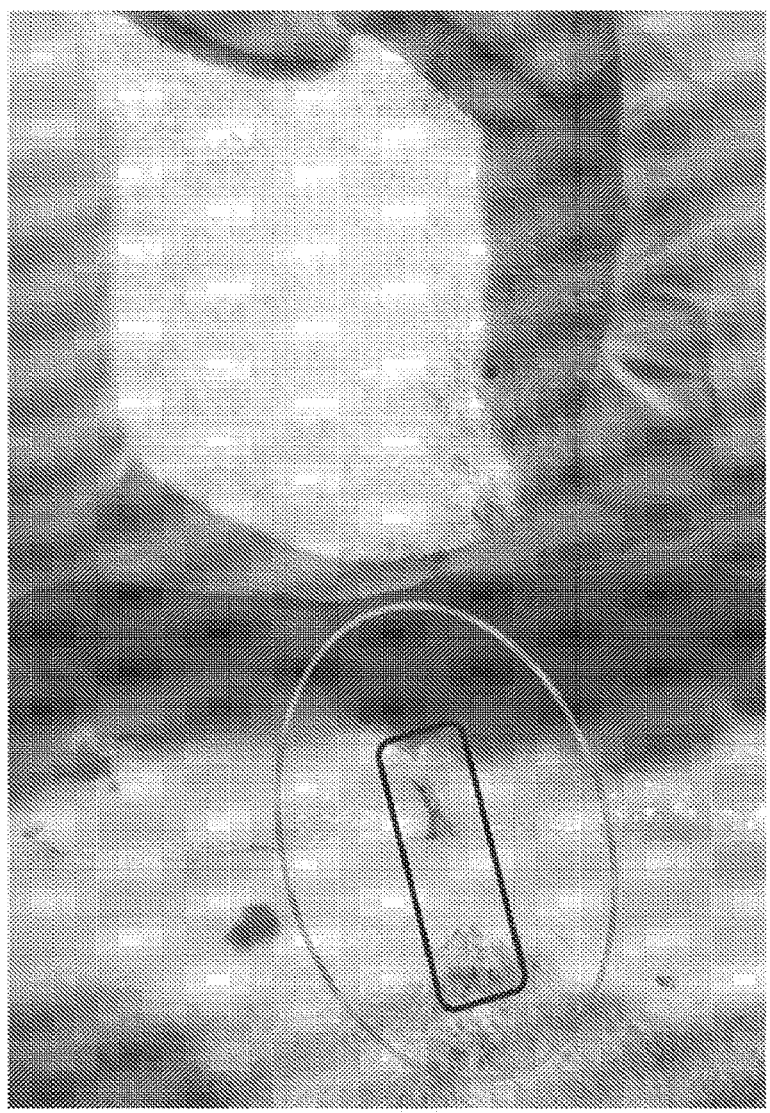
FIG. 2A-2C: Macroscopic view of the scars at time of 2 months sacrifice of a pig treated with Kythera.
Figure 2B:
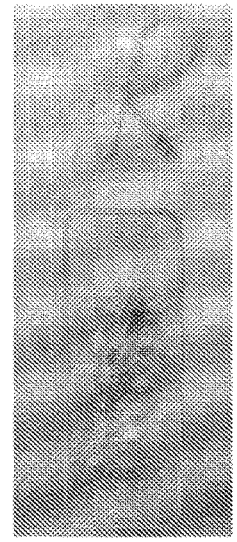
Figure 2C:
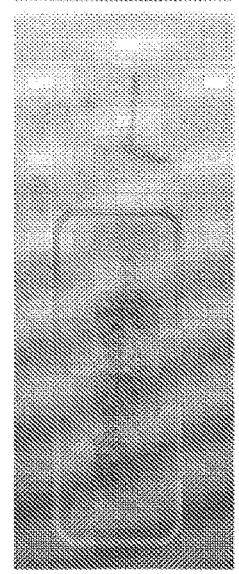

FIGS. 1 and 2 show a macroscopic view of the scars at time of 2 months sacrifice. As can be seen, the scar at the left, non-treated side, is much finer in RZL-012 of the invention treated pig, compared with Kythera treated pig. Also, after a cross section through the scar, a white scar tissue is clearly evident at the Kythera treated pig (surrounded by black rectangle) while no apparent scare tissue was observed in the carbazole derivative of the invention treated pig. It can be clearly be seen that scar formed at the non-treated side of the RZL-012 treated pig is much finer than the corresponding scar of the Kythera treated pig (FIG. 1C vs. FIG. 2C).

Figures 3A, 3B, 3C, 3D:
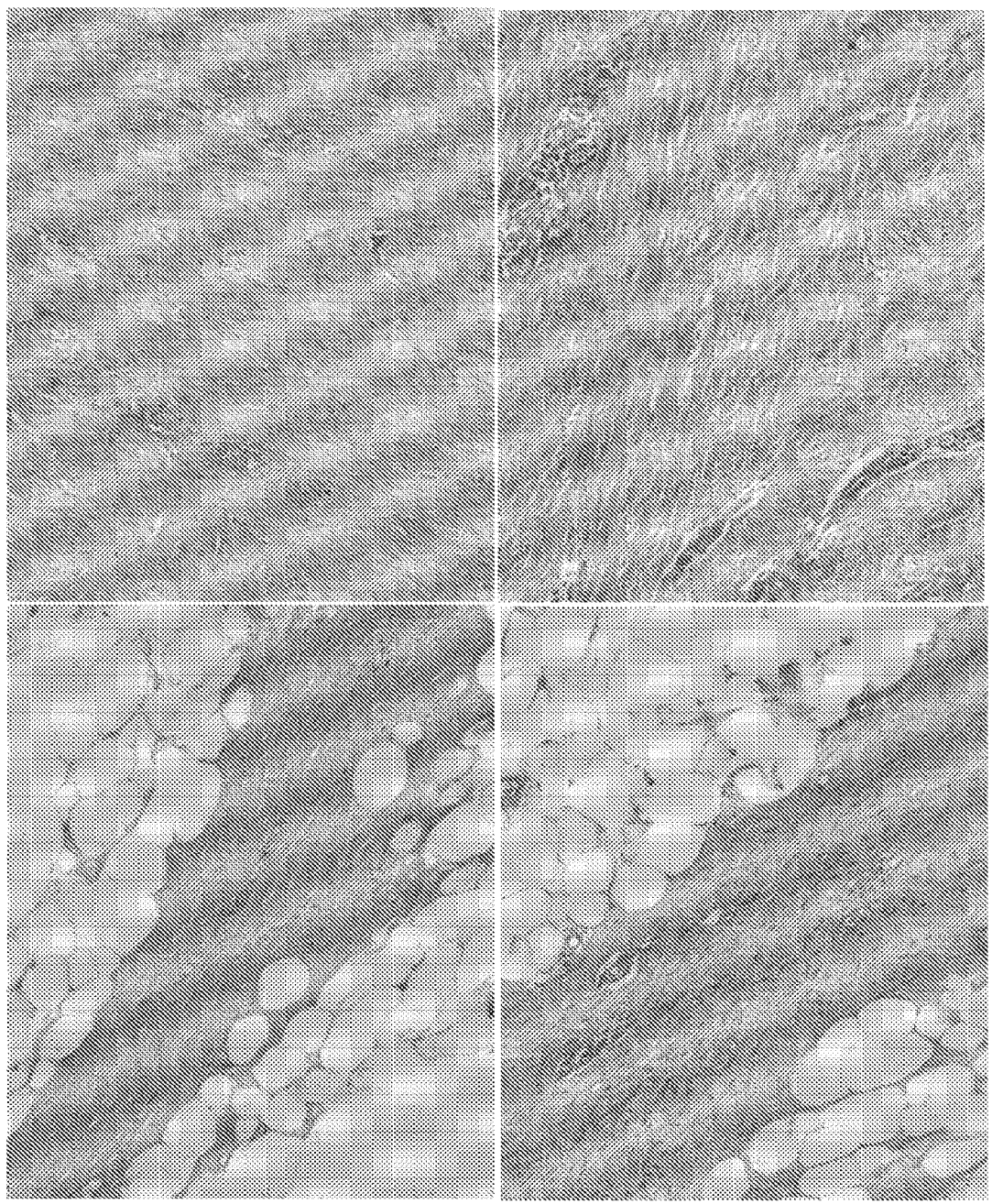
FIGS. 3A-3D: Scar Histology. H & E staining of cross-sections of the various scare tissues. X10 objective magnification.
Figures 4A, 4B, 4C, 4D:
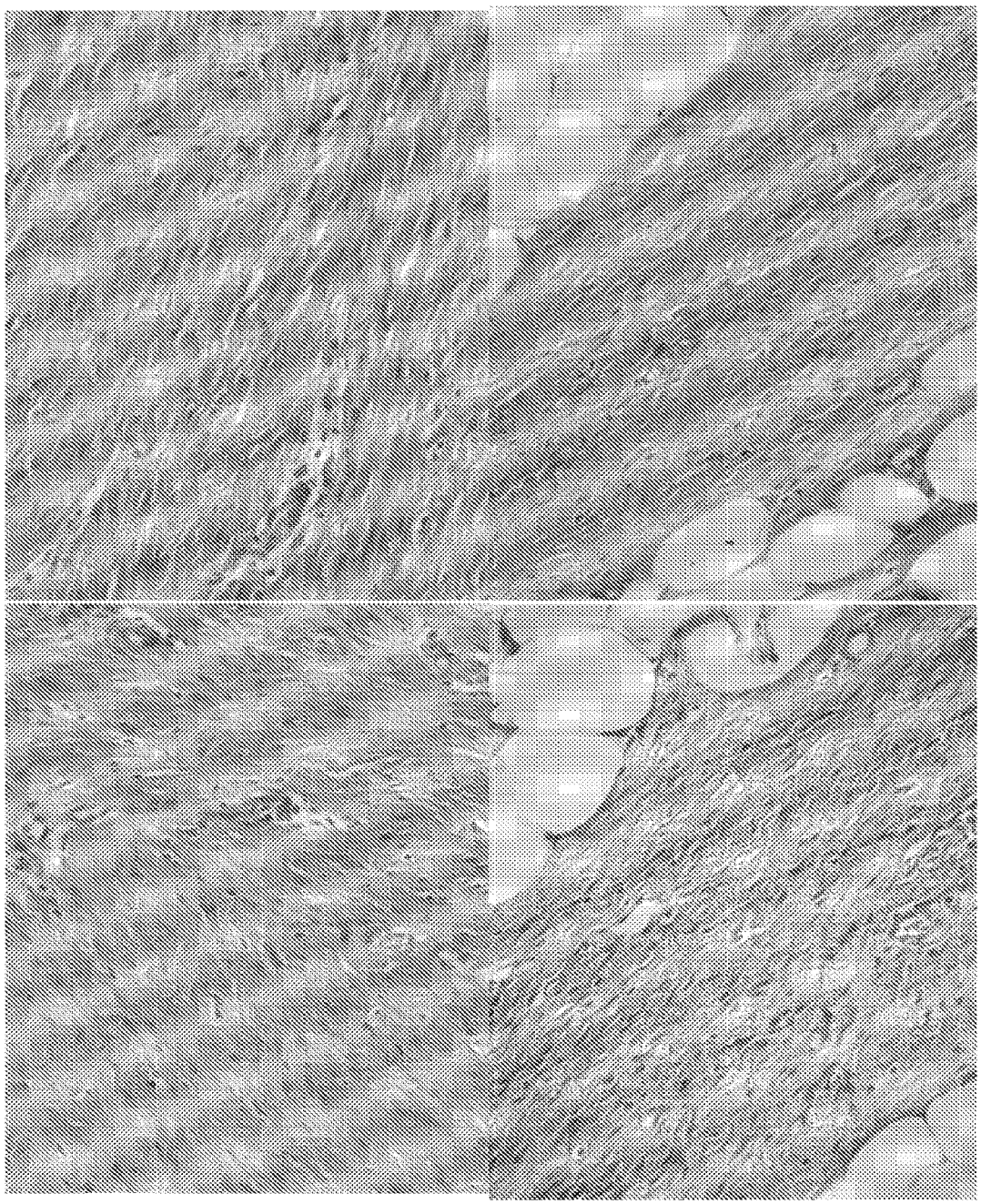
FIGS. 4A-4D: Scar Histology. H & E staining of cross-sections of the various scare tissues. X20 objective magnification.
Figures 5A, 5B, 5C, 5D:
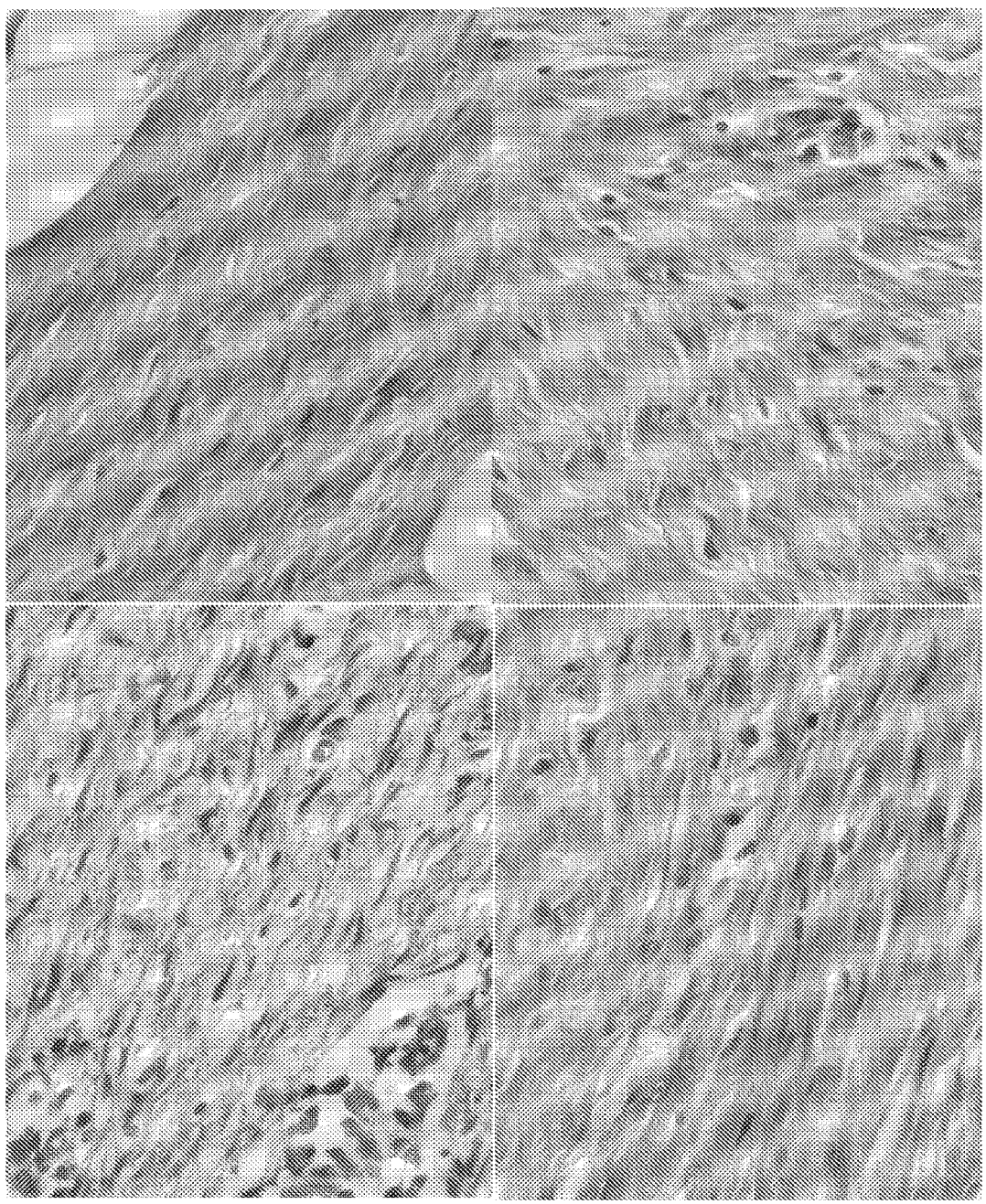
FIGS. 5A-5D: Scar Histology. H & E staining of cross-sections of the various scare tissues. X40 objective magnification.

FIG. 3A-3D shows the scar histology (H & E staining of cross-sections of the various scare tissues; X10 objective magnification). In agreement with the macroscopic view, the width of fibrotic tissue on both sides of the RZL-012 of the invention treated pig are much thinner (FIGS. 3A-3B) than those of the Kythera treated pig (FIGS. 3C-3D). Careful measurement reveals 4-5 times difference in the scar tissue width.

FIG. 4A-4D shows the scar histology of the same preparations as in FIG. 3 but at X20 objective magnification. It can be clearly seen that the scar-tissue in RZL-012 of the invention treated side (FIGS. 4A-4B) contains less collagen fibers as compared with the scar tissue of FIGS. 4C-4D.

FIG. 5A-5D shows the scar histology of the same preparations as in FIG. 3 but at X40 objective magnification. It can be clearly seen that the scar-tissue in RZL-012 of the invention treated side (FIGS. 5A-5B) contains less collagen fibers as compared with the scar tissue of FIGS. 5C-5D.

Example 2

Inhibition of Kidney Fibrosis by RZL-012

Animals: Male SD Rats, 250 g.

Induction of kidney fibrosis: Overnight fasted rats were anesthetized (a mixture of Ketamine 20 mg/kg and Xylazin 2 mg/kg IP). The abdominal cavity was exposed via a midline incision up to 0.5-1 cm before penis about 3 cm along. Then the bladder was lifted out and epididymal fat was remoted. The left ureter was ligated at two points with 4-0 sutures. The wound was closed in layers with the same sutures. Then animals were returned to the cages. This unilateral uretral ligation led to urine accumulation in the affected kidney, resulting in massive tissue fibrosis.

Treatment: Test (RZL-012 15 mg) and reference (Vehicle) articles were injected at Day 14 and Day 42, following UUO, subcutaneously into the dorsal bilateral inguinal fat layer and the nape-of-the-neck fat, using a 27 G ½" needle at a dose volume of 0.1 ml/site.

Tissue processing: 8 weeks after UUO the rats were sacrificed and the kidneys were removed, fixed and processed for histological examination. The tissue sections were stained with Masson-Trichrome which enable a distinction between fibrotic tissue (staining collagen fiber in Blue) and normal viable tissue (Purple-Red) (see FIG. 6C).

Figure 6A:
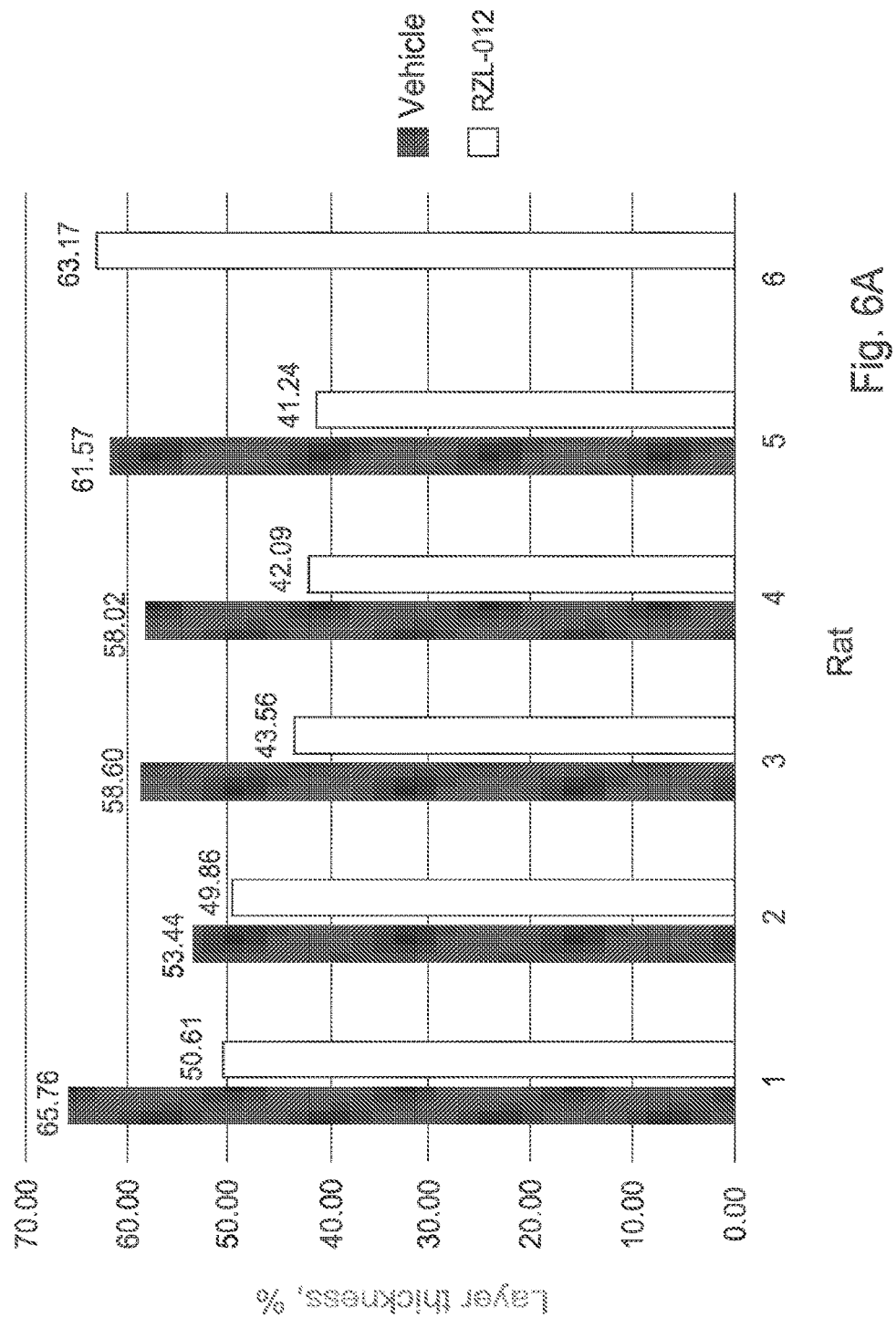
Figure 6C:
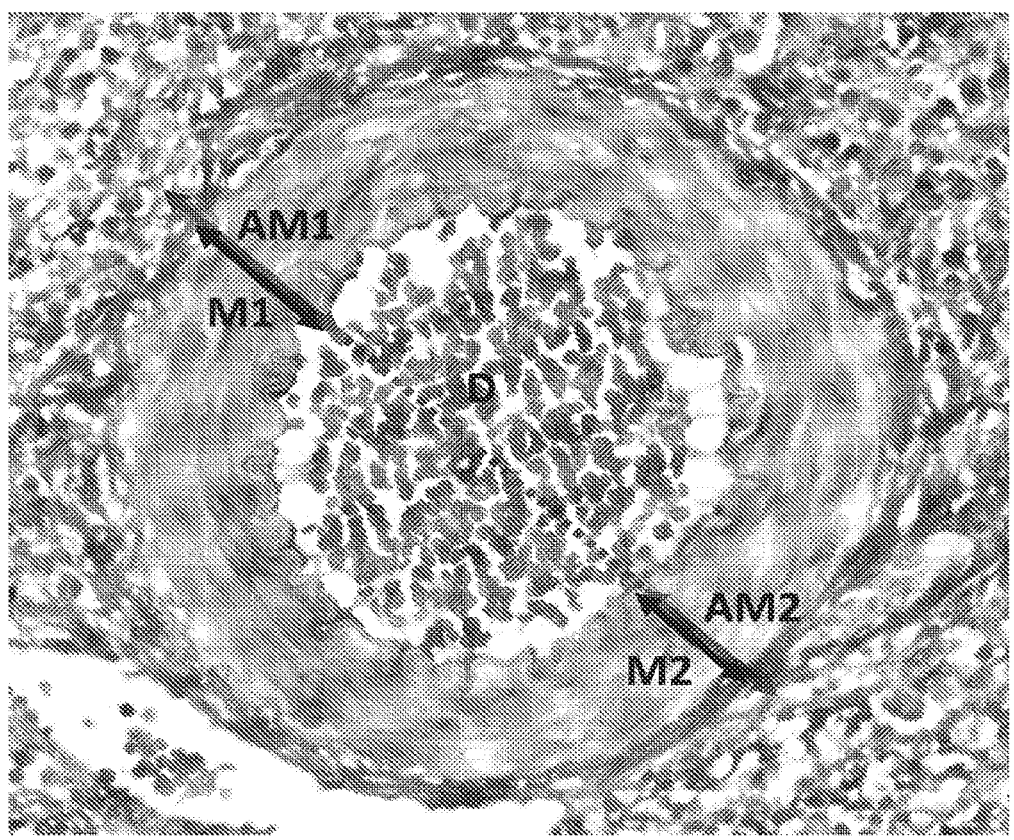

Quantification of kidney fibrosis: In order to quantify, in an unbiased way, the fibrotic response in RZL-treated vs. non-treated rats, the dimensions of the fibrotic layer surrounding aortic blood vessel, were measured. All aortic vessels in each affected kidney were analyzed in the following way: The vessel wall consists of two components, the usual Muscular layer and an outer layer, excessively rich in collagen, in these kidneys, hereby defined as "Adventitia" (FIG. 6C). The net width of the adventitia and that of the Muscular layer were calculated as follows:

$$\text{Adventitia layer} = \frac{(AM1 - M1) + (AM2 - M2)}{2}$$

$$\text{Muscular layer} = \frac{M1 + M2}{2}$$

By using the ratio between Adventitia and Muscular layers, the difference among vessels diameter was normalized.

Results: A total of 6 RZL-012 treated kidneys and 5 Vehicle kidneys were analyzed. The detailed results are depicted in FIG. 6A and the cumulative statistical analysis demonstrated a significant inhibition of kidney fibrosis by RZL-012 (FIG. 6B)

The invention claimed is:

1. A pharmaceutical composition comprising:
   (a) at least one active agent having the general formula (I) or any salt thereof

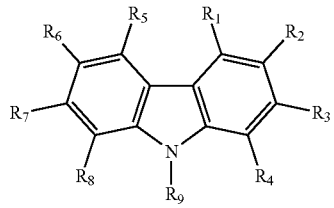

(I)

wherein
each of $R_1$-$R_8$ is independently selected from the group consisting of H, OH, SH, halogen, nitro, amino, nitrilo, nitroso, acetyl, acetamido, acylamido, alkylamino, straight or branched $C_1$-$C_5$ alkyl, straight or branched $C_2$-$C_5$ alkenyl, straight or branched $C_2$-$C_5$ alkynyl, amine, straight or branched $C_1$-$C_5$ alkoxy, straight or branched $C_1$-$C_5$ carboxyl, straight or branched $C_1$-$C_5$ ester, straight or branched $C_1$-$C_5$ thioxy, straight or branched $C_1$-$C_5$ sulfinyl, and straight or branched $C_1$-$C_5$ thionyl;
$R_9$ is selected from straight or branched $C_1$-$C_9$ alkyl, straight or branched $C_2$-$C_9$ alkenyl, straight or branched $C_2$-$C_9$ alkynyl, piperazinyl, pyridinyl, piperidinyl, morpholinyl and thiomorpholinyl, wherein $R_9$ is substituted with at least one quaternary amino (ammonium) group or a phosphonium group;
   (b) polysorbate 80;
   (c) propylene glycol;
   (d) benzyl alcohol; and
   (e) water.

2. The composition according to claim 1, wherein the composition comprises water content of less than 50% of total composition weight.

3. The composition according to claim 1, wherein the composition comprises water content of less than 30% of total composition weight.

4. The composition according to claim 1, wherein the composition comprises water content of about 25% of total composition weight.

5. The composition according to claim 1, wherein the composition comprises at least 0.1% by weight of said at least one active agent of total composition.

6. The composition according to claim 1, wherein the composition comprises between about 1% to about 5% by weight of said at least one active agent of total composition.

7. The composition according to claim 1, wherein the composition comprises about 5% by weight of said at least one active agent of total composition.

8. The composition according to claim 1, wherein the active agent is 3-(3,6-dibromo-9H-carbazol-9-yl)-N,N,N-trimethylpropan-1-aminium or a salt thereof.

9. The composition according to claim 1, wherein the composition is formulated for parenteral injection.

10. The composition according to claim 1, comprising:
    about 5-5.6% by weight of 3-(3,6-dibromo-9H-carbazol-9-yl)-N,N,N-trimethylpropan-1-aminium or a salt thereof;
    about 10% by weight of polysorbate 80;
    about 57% of propylene glycol;
    about 3% by weight of benzyl alcohol; and
    about 24.4-25% by weight water for injection;
    wherein % by weight is based on total weight of the composition.

* * * * *